(12) United States Patent
Matsumoto

(10) Patent No.: US 6,973,160 B2
(45) Date of Patent: Dec. 6, 2005

(54) X-RAY-TOMOGRAPHIC IMAGING APPARATUS, X-RAY-TOMOGRAPHIC IMAGING METHOD, AND PROGRAM

(75) Inventor: Kazuhiro Matsumoto, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 124 days.

(21) Appl. No.: 10/705,910

(22) Filed: Nov. 13, 2003

(65) Prior Publication Data

US 2004/0101092 A1 May 27, 2004

(30) Foreign Application Priority Data

Nov. 26, 2002 (JP) .............................. 2002-342774

(51) Int. Cl.[7] .............................................. H05G 1/64
(52) U.S. Cl. .......................... 378/22; 378/21; 378/24; 378/98.8; 378/197
(58) Field of Search ........................... 378/21–27, 98.8, 378/197

(56) References Cited

U.S. PATENT DOCUMENTS

| | | | | |
|---|---|---|---|---|
| 4,095,110 | A | * | 6/1978 | Bunch .......................... 378/26 |
| 5,528,043 | A | * | 6/1996 | Spivey et al. .......... 250/370.09 |
| 5,812,191 | A | * | 9/1998 | Orava et al. ................. 348/308 |
| 5,872,828 | A | * | 2/1999 | Niklason et al. ............... 378/23 |
| 6,069,933 | A | * | 5/2000 | Schultz ......................... 378/62 |
| 6,341,156 | B1 | * | 1/2002 | Baetz et al. ................ 378/98.8 |
| 6,411,674 | B1 | * | 6/2002 | Oikawa ....................... 378/21 |
| 6,501,829 | B2 | | 12/2002 | Matsumoto et al. ........ 378/154 |
| 6,643,351 | B2 | * | 11/2003 | Morita et al. .................. 378/4 |
| 2002/0024601 | A1 | | 2/2002 | Kaifu et al. |

FOREIGN PATENT DOCUMENTS

| | | |
|---|---|---|
| GB | 2 371 196 | 7/2002 |
| JP | 7-171142 | 7/1995 |
| JP | 2610438 | 2/1997 |
| JP | 11-99146 | 4/1999 |

* cited by examiner

*Primary Examiner*—Allen C. Ho
(74) *Attorney, Agent, or Firm*—Fitzpatrick, Cella, Harper & Scinto

(57) ABSTRACT

An X-ray-tomographic imaging apparatus for obtaining image data on a predetermined tomographic section of a subject with efficiency and effectiveness by using a plurality of X-ray projection images achieved by a plurality of X-rays that is made incident on the tomographic section from different directions is provided. The X-ray-tomographic imaging apparatus comprises a solid-image pickup unit that can convert each of the X-ray projection images to a signal and read the signal by a non-destructive reading method and a control unit making the solid-image pickup unit accumulate the signals of the X-ray projection images and read the signals by the non-destructive reading method during the signal accumulation.

2 Claims, 9 Drawing Sheets

X-RAY-TOMOGRAPHIC IMAGING APPARATUS, X-RAY-TOMOGRAPHIC IMAGING METHOD, AND PROGRAM

BACKGROUND OF THE INVENTION

1. Field of the Invention

The present invention relates to an X-ray-tomographic imaging apparatus, an X-ray-tomographic imaging method, and a program.

2. Description of the Related Art

Hitherto, X-ray-tomographic imaging has been performed by using an X-ray film. Typically, a subject is placed between an X-ray tube and the X-ray film. X-ray exposure is performed a plurality of times while the X-ray tube and the X-ray film are moved in opposite directions, with respect to the subject, in synchronization, so that the center of the X-ray beam and the center of the X-ray film are aligned. Subsequently, an X-ray-transmission image is obtained each time the X-ray exposure is performed. Further, multiple exposures of the X-ray-transmission images are performed on one film, whereby the image of a tomographic section of the subject is obtained. In this tomographic-section image, constitutional elements of the subject at a predetermined distance from the tomographic section become blurred.

Further, digital-tomographic imaging apparatuses have been commercially introduced. In this case, the addition of a predetermined item of digital image data to another predetermined item of the digital image data is performed by using an image intensifier (hereinafter referred to as an I.I.) and a TV-imaging system that are used in place of the X-ray film. Subsequently, a reorganized image is obtained. This reorganized image is equivalent to the above-described tomographic-section image obtained in the case where the multiple exposures are performed on the film.

Japanese Patent Laid-Open No. 7-171142 discloses a radiodiagnostic device, including a solid-image pickup element that can perform non-destructive reading. This radiodiagnostic device can stop X-ray exposure based on the pixel value of an image obtained by the non-destructive reading. Further, the radiodiagnostic device can read image information after the X-ray exposure is stopped, because the image information has been accumulated in the solid-image pickup element.

Japanese Patent No. 2610438 discloses a method of driving a solid-image pickup device, including an image sensor that can perform non-destructive reading. This solid-image pickup device removes fixed-pattern noise through the non-destructive reading.

In the past, in the case where known analog imaging is performed by using an X-ray film as an image-pickup system, the X-ray tube and the X-ray film move in a predetermined orbit in a predetermined range. That is to say, the range in which the X-ray tube and X-ray film move is already determined before the tomographic imaging is performed. Therefore, if a user wishes to obtain a tomographic image in a different moving range, the user has to perform tomographic imaging again.

In this case, it is impossible for the user to observe an obtained tomographic image soon after the imaging is finished.

Further, in the case where known digital-tomographic imaging is performed by using the I.I. and a TV-image-pickup system as the image-pickup system, it becomes possible to reorganize a tomographic image by using predetermined parts of the image data after the digital-tomographic imaging is finished. In this case, the predetermined part of the image data corresponds to a predetermined part of the range in which the X-ray tube and the image-pickup system move in a predetermined orbit. In this case, however, it must be arranged so that calculation is performed as many times as the number of items of image data required for the reorganization. Therefore, it is impossible to display the reorganized tomographic image soon after the tomographic imaging is finished. Further, since the tomographic imaging is performed a plurality of times in sequence, image information of a previous frame (electrical charges) often affects image information of the next frame, whereby the quality of the reorganized tomographic image is deteriorated. Further, it must be arranged so that all the data on a plurality of images obtained by the tomographic imaging is stored for the tomographic-image reorganization. Therefore, very large frame-memory capacity is required.

SUMMARY OF THE INVENTION

Accordingly, it is an object of the present invention to obtain the image data on a tomographic section of a subject with efficiency and effectiveness.

According to one respect of the present invention, the foregoing object is attained by providing an X-ray-tomographic imaging apparatus comprising an X-ray generation unit for applying an X-ray, a first moving unit for changing a direction in which the X-ray generation unit applies the X-ray and making the X-ray generation unit move, a solid-image pickup unit that includes a plurality of solid-image pickup elements and that converts the X-ray into at least one electrical signal, a second moving unit for making the solid-image pickup unit move, and a control unit that controls the first moving unit and the second moving unit so that the X-ray generation unit applies the X-ray to predetermined coordinates on a light-receiving surface of the solid-image pickup unit and that controls X-ray application performed by the X-ray generation unit and driving of the solid-image pickup unit. The control unit controls the driving of the solid-image pickup unit so that the solid-image pickup unit accumulates and keeps at least one electrical charge while the X-ray generation unit repeats the X-ray application a predetermined number of times, or over a predetermined period of time.

In a preferred aspect, the control unit further controls the driving of the solid-image pickup unit so that the solid-image pickup unit accumulates and keeps the electrical charge over a predetermined period of time during which the X-ray generation unit and/or the solid-image pickup unit move.

In a yet another preferred aspect, the control unit further controls the driving of the solid-image pickup unit so that the solid-image pickup unit discharges the electrical charge after the X-ray application is repeated a predetermined number of times or a predetermined period of time passes.

In still another preferred aspect, the X-ray-tomographic imaging apparatus also includes an analog-to-digital conversion unit for analog-to-digital conversion of an output from the solid-image pickup unit into image data, a storage unit for keeping the image data that is output from the analog-to-digital conversion unit at predetermined time intervals, and a gray-scale adjuster unit for performing gray-scale conversion for the image data stored in the storage unit by using a predetermined gray-scale conversion function.

In another preferred aspect, the gray-scale conversion function is determined, based on the maximum value and minimum value of the image data.

In yet another preferred aspect, the X-ray-tomographic imaging apparatus also includes a display unit for displaying an image subjected to the gray-scale conversion by the gray-scale adjuster.

In another preferred aspect, the X-ray-tomographic image apparatus also includes an analog-to-digital conversion unit for analog-to-digital converting of an output from the solid-image unit into image data, a storage unit for keeping the image data that is output from the analog-to-digital conversion at predetermined time intervals, and a projection-image generation unit for subtracting two items of image data from the image data stored in the storage unit.

According to another embodiment of the invention, there is provided an X-ray-tomographic imaging apparatus for obtaining image data of a predetermined tomographic section in a subject by using a plurality of X-ray projection images achieved by a plurality of X-rays that is made incident on the predetermined tomographic section from different directions, which includes a solid-image pickup unit that can convert each of the X-ray projection images to a signal and read the signal in a non-destructive reading manner, and a control unit from making the solid-image pickup unit accumulate the signals of the X-ray projection images and read the signals in a non-destructive reading manner during the signal accumulation.

In another embodiment of the invention, there is provided an X-ray-tomographic imaging method used for an X-ray-tomographic imaging apparatus have a solid-image pickup unit that can convert an X-ray projection image to a signal and read the signal in a non-destructive reading manner. The X-ray-tomographic imaging apparatus is provided for obtaining image data of predetermined tomographic section in a subject by using a plurality of X-ray projection images achieved by a plurality of X-rays that is made incident on the predetermined tomographic section from different directions. The X-ray image method includes the steps of performing accumulation control for making the solid-image pickup unit accumulate the signal of each of the X-ray projection images, and performing read control for making the solid-image pickup unit read the signal in a non-destructive reading manner during the signal accumulation.

In a preferred aspect of the invention, there is provided a program that can be executed by an information processing apparatus having program code for practicing the X-ray-tomographic imaging method described above.

Other objects, features and advantages of the present invention will become apparent from the following preferred embodiments with the accompanying drawings, in which like reference characters designate the same or similar part through the drawings thereof.

BRIEF DESCRIPTION OF THE DRAWINGS

The accompanying drawings, which are incorporated in and constitute a part of the specification, illustrate embodiments of the invention and, together with the descriptions, serve to explain the principle of the invention.

DESCRIPTION OF THE PREFERRED EMBODIMENTS

Preferred embodiments of the present invention will be described in detail in accordance with the accompanying drawings.

An X-ray-digital-tomographic imaging apparatus (an X-ray-tomographic imaging apparatus), an X-ray-digital-tomographic imaging method (an X-ray-tomographic imaging method), and an X-ray-digital-tomographic imaging program according to embodiments of the present invention will be described in detail.

(First Embodiment)

Figure 1:
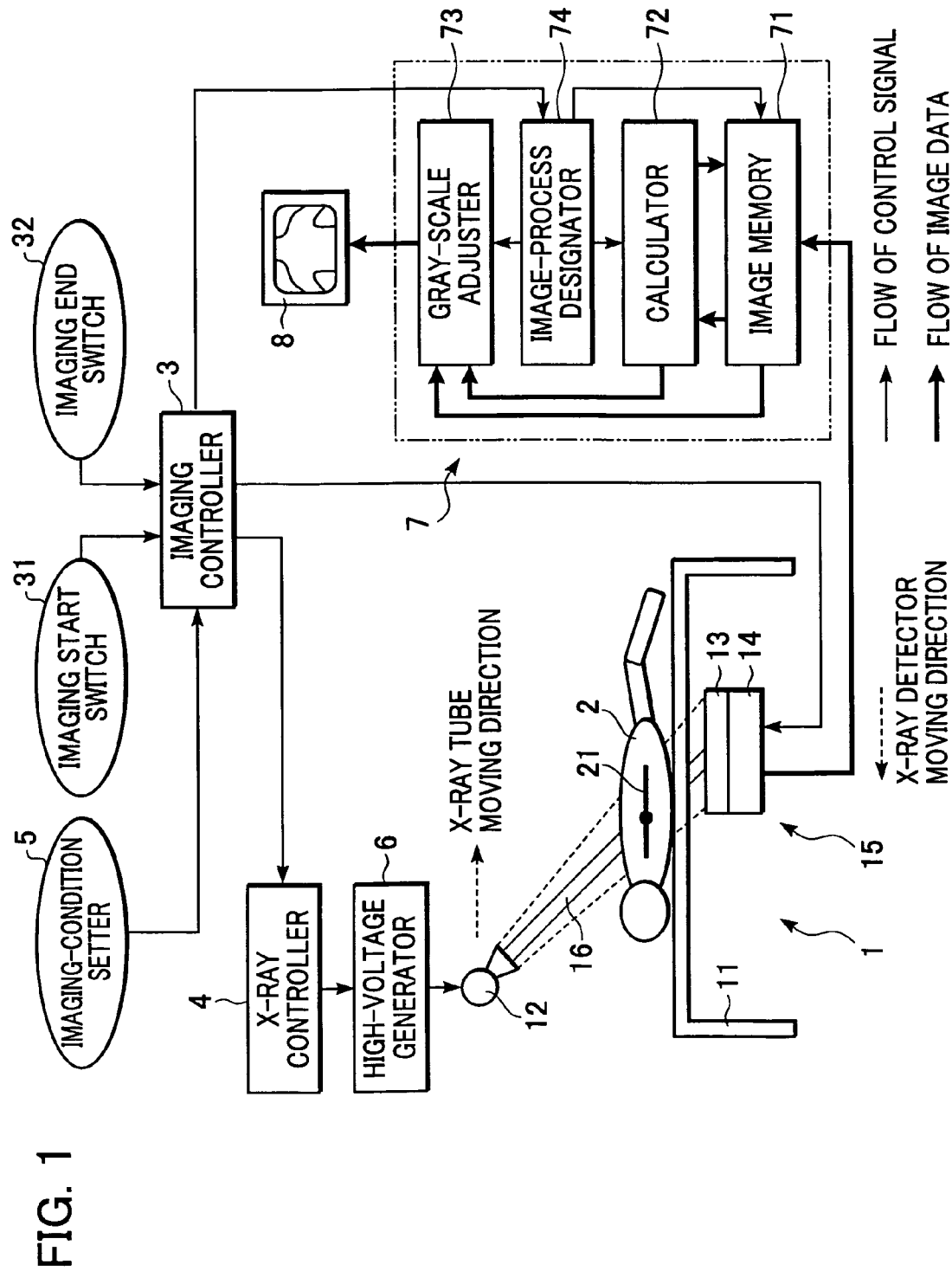
FIG. 1 is a block diagram illustrating the schematic configuration of an X-ray-digital-tomographic imaging apparatus according to a first embodiment of the present invention.

A first embodiment of the present invention will now be described with reference to FIG. 1.

In the case of this X-ray-digital-tomographic imaging apparatus, a subject 2 is placed on a bed 11. An X-ray tube 12 is provided at a predetermined position above the bed 11. An X-ray detector 15 accommodated in a case (not shown) is provided under the bed 11. This X-ray detector 15 includes, for example, a solid-image pickup unit 13 and an image-pickup drive unit 14. This image-pickup drive unit 14 reads an X-ray image of the subject 2, as an electrical signal, by driving the solid-image pickup unit 13, and generates digital image data. The X-ray tube 12 and the X-ray detector 15 are coupled to each other by a rocking lever 16. Subsequently, the X-ray tube 12 and the X-ray detector 15 can move in parallel and in opposite directions with respect to a predetermined position on a tomographic section 21. The predetermined position is provided inside the subject 2. The above-described elements are included in a tomographic imaging table 1.

The X-ray-digital-tomographic imaging apparatus further has an imaging controller 3, an X-ray controller 4, an imaging-condition setter 5, a high-voltage generator 6, a signal-processing device 7, and an image display monitor 8.

The imaging controller 3 transmits an instruction to each of the tomographic imaging table 1, the X-ray controller 4, and so forth, so as to control a series of processing procedures of tomographic imaging. More specifically, for example, the imaging controller 3 controls the movement of the X-ray tube 12 and the X-ray detector 15 during the tomographic imaging. Further, for example, the imaging controller 3 transmits a signal to the X-ray controller 4 and another signal to the image-pickup drive unit 14, respectively, so as to control the timing of X-ray exposure and image-data reading. An imaging start switch 31 and an imaging end switch 32 are connected to the imaging controller 3. The imaging controller 3 can be formed as a computer, for example, where the computer operates based on an X-ray-digital-tomographic imaging program for performing processing procedures that will be described later.

The imaging-condition setter 5 is connected to the imaging controller 3 and can set various imaging conditions according to operations performed by an operator. The X-ray controller 4 controls the high-voltage generator 6, based on the set imaging conditions, and a voltage is applied from the high-voltage generator 6 to the X-ray tube 12. Subsequently, a predetermined X-ray is applied from the X-ray tube 12. The movement of the X-ray tube 12 and the X-ray detector 15 is controlled by the imaging controller 3, and is executed based on the imaging conditions set by the imaging-condition setter 5.

The signal-processing device 7 has an image memory 71, a calculator 72, a gray-scale adjustor 73, and an image-process designator 74. The digital image data output from the X-ray detector 15 is transmitted to the signal-processing device 7 and stored in the image memory 71. A monitor 8 for image display is connected to the signal-processing device 7. The calculator 72 performs calculations such as addition, subtraction, and so forth, for the image data. The gray-scale adjustor 73 adjusts the gray scale of an image displayed on the monitor 8. The image-process designator 74 controls the image memory 71, the calculator 72, and the gray-scale adjustor 73, based on the instruction transmitted from the imaging controller 3. The image-process designator 74 controls the image memory 71 and the calculator 72, for example, for selecting predetermined data from among image data stored in the image memory 71. The calculator 72 can perform subtraction and/or addition for each pixel between and/or among the selected image data. The result of this calculation can be displayed on the monitor 8 and stored in the image memory 71 again.

Figure 2:
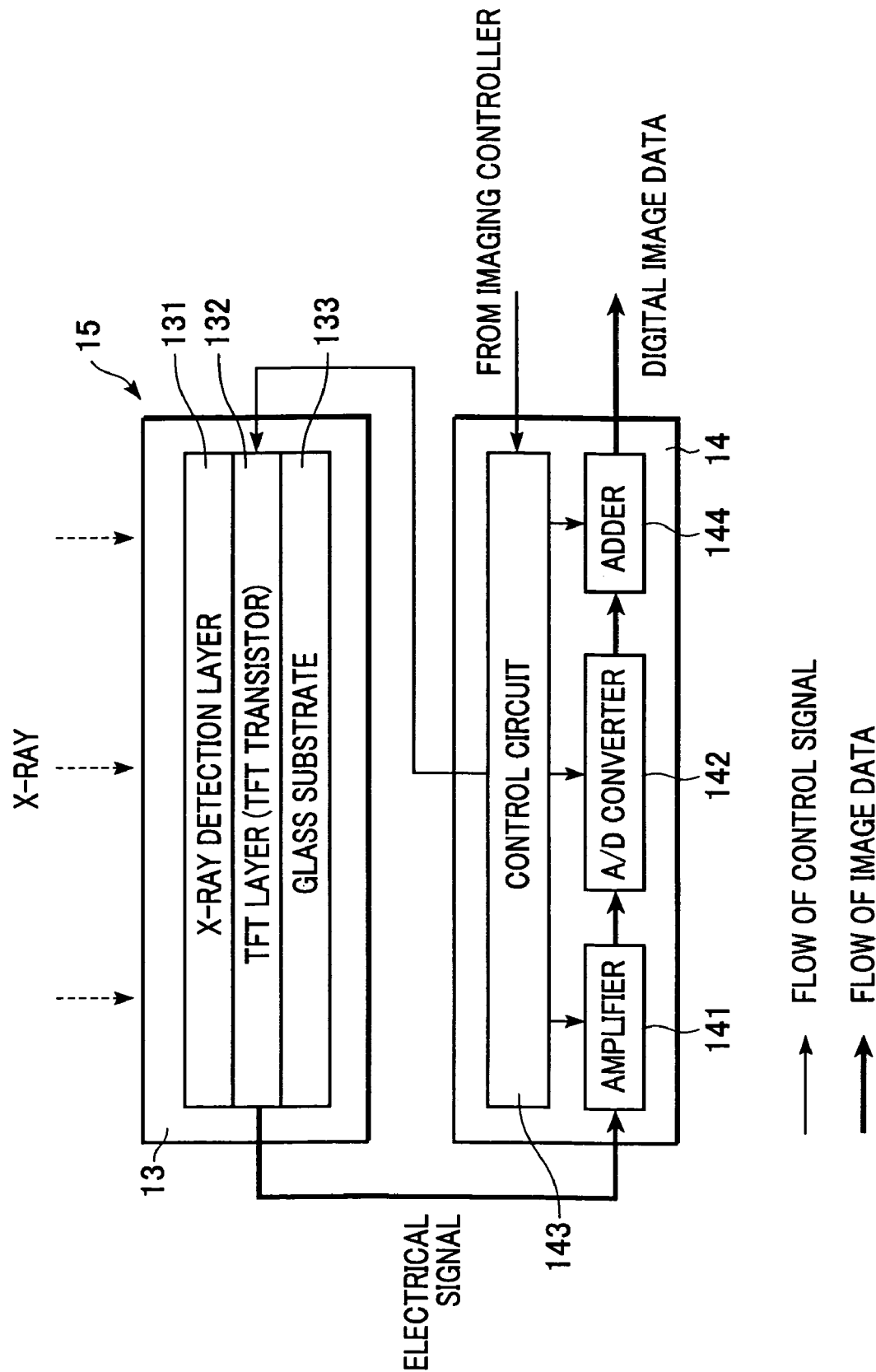
FIG. 2 is a schematic diagram showing the configuration of an X-ray detector.

FIG. 2 is a schematic diagram illustrating the configuration of the X-ray detector 15. The solid-image pickup unit 13 has a flat-panel shape, for example. As shown in this drawing, the solid-image pickup unit 13 has an X-ray detection layer 131 including a photoelectric conversion unit for converting an X-ray passed through the subject 2 into an electrical charge and a thin-film transistor layer 132 (hereinafter referred to as a TFT layer). This TFT layer 132 includes a TFT formed in matrix form, the TFT being provided for reading at least one electrical charge generated in the X-ray detection layer 131. The X-ray detection layer 131 and the TFT layer 132 are provided on a glass substrate 133.

The image-pickup drive unit 14 has an amplifier 141 for amplifying an electrical signal read via the TFT layer 132, an A/D converter 142 for converting an output signal (an analog signal) from the amplifier 141 to a digital signal, a control circuit 143, and an adder 144 for adding frame numbers, or the like, to the digital signal converted by the A/D converter 142. The above-described elements of image-pickup drive unit 14 generate digital image data and output that the digital image data. The control circuit 143 controls switching of each of the TFTs in the TFT layer 132 for reading electrical charges in sequence, where the electrical charges are generated in the X-ray detection layer 131 by X-ray irradiation. The control circuit 143 further controls the operation of the A/D converter 142, the adder 144, and the gain of the amplifier 141. Each of the above-described image-pickup drive unit 14 and the solid-image pickup unit 13 is accommodated in a cabinet, so as to form the X-ray detector 15.

The X-ray detection layer 131 includes a cesium iodide layer (hereinafter referred to as a CsI layer) and a photo-diode layer, for example. When an X-ray is made incident on the X-ray detection layer 131, the X-ray is converted to fluorescence in the CsI layer. The converted light is guided by the CsI with a columnar crystal structure to a lower layer. That lower layer is the photo-diode layer. The photo-diode layer has photo diodes corresponding to pixels, and the photo diodes are provided in matrix form.

In each of the photo diodes, light is converted to an electrical charge. The converted electrical charges are accumulated in a capacitor or the like. The accumulated electrical charges are read as electrical signals in sequence for each pixel via the TFTs in the TFT layer 132. The solid-image pickup unit 13 can perform non-destructive reading and destructive reading. More specifically, the solid-image pickup unit 13 can read the accumulated electrical charges while substantially keeping them. That is to say, the solid-image pickup unit 13 can read the accumulated electrical charges without discharging them. This reading method is referred to as the non-destructive reading. However, the solid-image pickup unit 13 can also read the accumulated electrical charges by discharging them. This reading method is referred to as the destructive reading. Further, under the control of the control circuit 143, it becomes possible to select and perform either the destructive reading or the non-destructive reading through the solid-image pickup unit 13.

When imaging is performed in the case where a solid-image pickup element that cannot perform the non-destructive reading is used, at least one electrical charge according to the quantity of incident light is accumulated in each pixel of the solid-image pickup element. When the accumulated electrical charge is taken out of the solid-image pickup element, as an electrical signal, no electrical charge to be taken out is left inside the solid-image pickup element. That is to say, after the electrical signal is read, another electrical charge to be taken out must be generated and accumulated in the pixel for the next reading.

In the case where a solid-image pickup element that can perform the non-destructive reading is used, an accumulated electrical charge is not taken out even though the accumulated electrical charge is read as an electrical signal. Therefore, it becomes possible to obtain an output proportional to electrical charges in pixels while continuing electrical-charge accumulation.

The operation of the above-described X-ray-digital-tomographic imaging apparatus of this embodiment will now be described.

As preparation for imaging, the operator sets tomographic imaging conditions through the imaging-condition setter 5 for obtaining a predetermined tomographic image for diagnosis. Main conditions among these are, for example, X-ray irradiation conditions relating to the tube voltage, the tube current, and the X-ray irradiation time, as well as imaging conditions relating to an imaging angle range, the number of images, and so forth.

Figure 3:
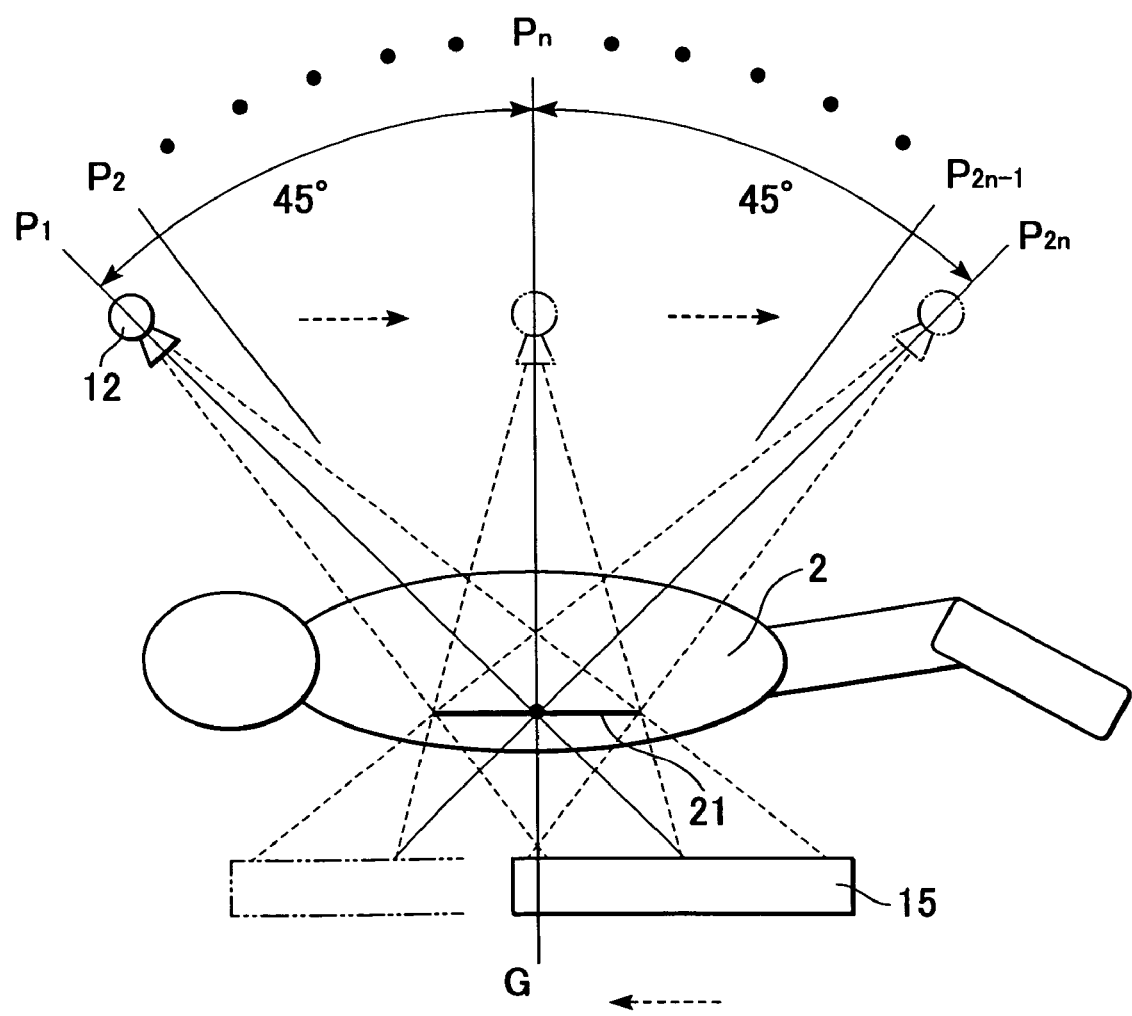
FIG. 3 is a schematic diagram illustrating example imaging conditions according to the first embodiment.

Under the imaging conditions of the first embodiment shown in FIG. 3, a vertical line G passing through the center of the tomographic section 21 is determined to be a center point. Further, a range from −45° to +45° of the subject 2 (in this case a human body) with respect to the center point along a vertical direction is determined to be the imaging angle range. That is to say, a 90°-angle range of the subject 2 is determined to be the imaging angle range. Relating to the position of the X-ray tube 12, or the X-ray irradiation angle, position $P_1$ is determined to be an imaging start point and position $P_{2n}$ is determined to be an imaging end point. Subsequently, tomographic imaging is started when the X-ray tube 12 is at the position $P_1$ and ended when the X-ray tube 12 reaches the position $P_{2n}$. During the tomographic imaging, the X-ray tube 12 passes position $P_n$. In the case where the above-described subject 2 is subjected to the tomographic imaging, an X-ray pulse is emitted from positions $P_1, P_2, \ldots, P_{2n-1}$, and $P_{2n}$. Each of the positions divides a segment from the position $P_1$ to the position $P_{2n}$ into $2_{n-1}$ equal portions. Subsequently, X-ray irradiation is performed 2n times. As shown in FIG. 3, the positions of the X-ray tube 12 are predetermined positions on the above-described segment, where the predetermined positions correspond to the X-ray irradiation angle.

The imaging angle range is determined according to the thickness of the tomographic section. The number of imaging is mostly determined according to the quality of a tomographic image. Further, the tube voltage and the tube current are mainly determined based on an imaging site. The tube current, the X-ray irradiation time, and the number of images are determined according to the interrelationships among them. This is because the maximum amount of electrical charges that can be accumulated in one pixel of the solid-image pickup unit 13 is fixed and the amount of electrical charges accumulated in the pixel by one X-ray application is mainly determined according to the tube current and the X-ray irradiation time. That is to say, it is impossible to obtain an effective tomographic image when a predetermined amount of X-rays are emitted, where the predetermined amount of X-rays is more than X-rays corresponding to the maximum amount of electrical charges that can be accumulated in one pixel. This configuration is the same as that in the case where the known analog-tomographic imaging is performed by using the X-ray film.

According to this embodiment, it is arranged that X-ray exposure is performed 2n times while the abdomen of the subject 2 is subjected to tomographic imaging, for example. The tube voltage V is determined to be $V_1$, the tube current I is determined to be $I_1$, and the X-ray irradiation time T is determined to be $T_1$. These conditions remain constant while the X-ray exposure is performed 2n times. Further, these conditions are determined so that a signal transmitted from the solid-image pickup unit 13 for each X-ray exposure is read by a non-destructive reading method.

Figure 4:
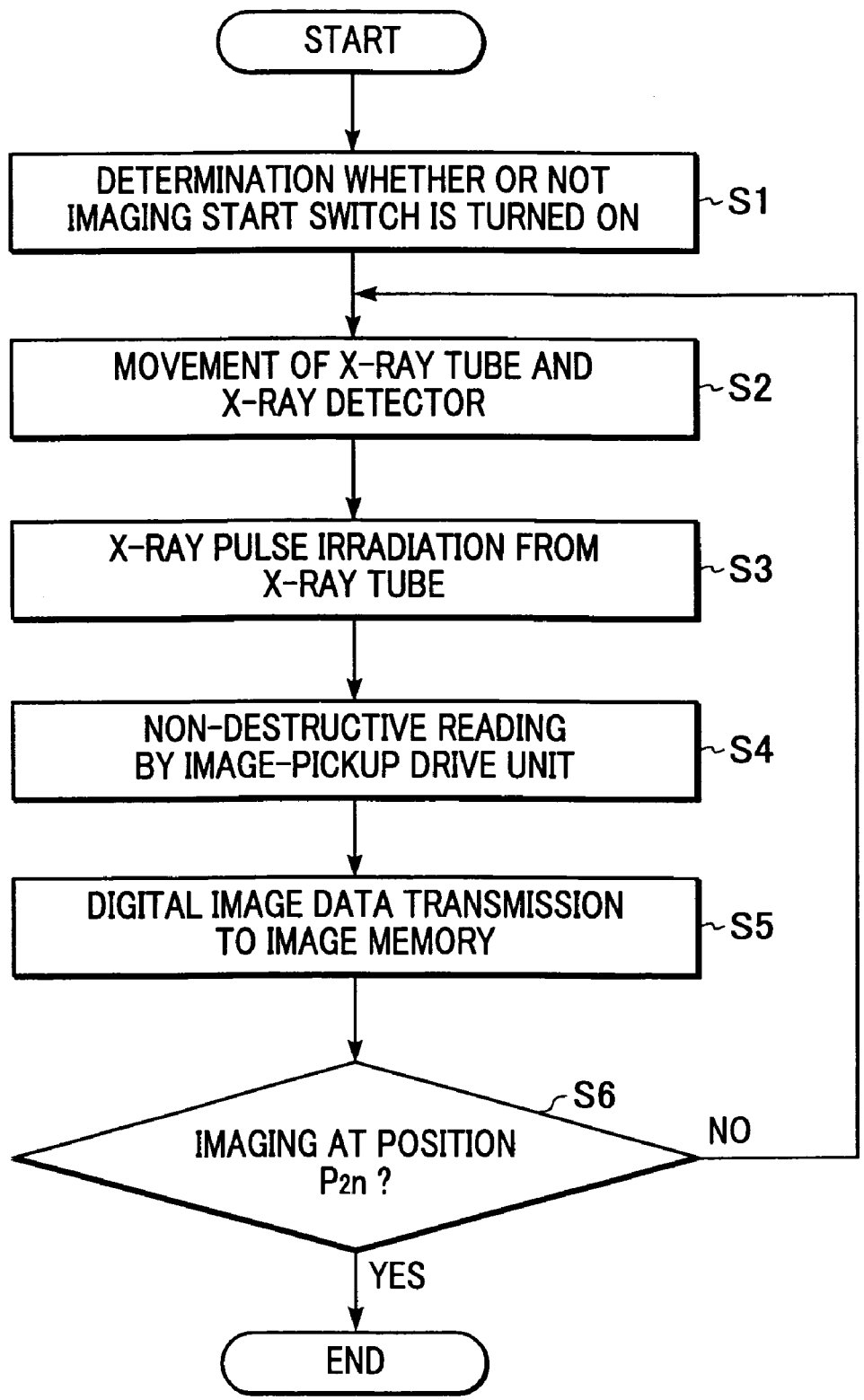
FIG. 4 is a flowchart illustrating an imaging method on the basis of the imaging conditions shown in FIG. 3.

Then, the tomographic imaging is started. FIG. 4 is a flowchart illustrating an imaging method according to the imaging conditions shown in FIG. 3. This tomographic imaging is performed under the control of the imaging controller 3. First, it is determined whether or not the operator turned on the imaging start switch 31. If the answer is yes, the process advances to step S2. In the case where the answer is no, the determination process at step S1 is repeated with predetermined timing (step S1). At step S2, the imaging controller 3 transmits an instruction necessary for imaging to each of the tomographic imaging table 1, the X-ray controller 4, and the image-pickup drive unit 14, for controlling the operations of these units. Here, a control signal is transmitted to the tomographic imaging table 1 for controlling a drive unit (not shown) provided in the tomographic imaging table 1, and the X-ray tube 12 and the X-ray detector 15, that are coupled to each other by the rocking lever 16, move from the position shown in FIG. 1 in a direction indicated by a broken-line arrow.

At step S3, information about the X-ray irradiation conditions and an imaging start signal are transmitted to the X-ray controller 4 in synchronization with the movement of the units near the tomographic imaging table 1. The X-ray controller 4 makes the high-voltage generator 6 operate so that the X-ray tube 12 applies an X-ray pulse generated in the case where the value of the tube voltage is $V_1$, the value of the tube current is $I_1$, and the value of the X-ray irradiation time is $T_1$.

Further, at step S4, the information about the imaging conditions, the imaging start signal, and so forth are transmitted to the control circuit 143 in the image-pickup drive unit 14. The control circuit 143 controls the operations of the units of the solid-image pickup unit 13 and those of the image-pickup drive unit 14 in synchronization with the above-described X-ray pulse application. When the X-ray pulse irradiation is ended, the control circuit 143 makes the switching elements in the TFT layer 132 operate and reads electrical charge distribution corresponding to an X-ray image obtained by X-rays passed through the subject 2.

As has been described, it is arranged that the reading is performed by the non-destructive reading method. Therefore, image signals $A_i$ ($1 \leq i \leq 2n$) corresponding to one frame are obtained by the non-destructive reading method, corresponding to the X-ray irradiation performed by the X-ray tube 12 at the position $P_i$ ($1 \leq i \leq 2n$).

At step S5, the read electrical signals are amplified according to a predetermined gain of the amplifier 141 and converted into digital signals by the A/D converter 142. The adder 144 applies information about frame number, the imaging conditions, and so forth, to the digital image signals corresponding to one frame, whereby digital image data $D_i$ ($1 \leq i \leq 2n$) is generated. The digital image data $D_i$ is transmitted to an image memory 71 and stored therein.

Figure 5:
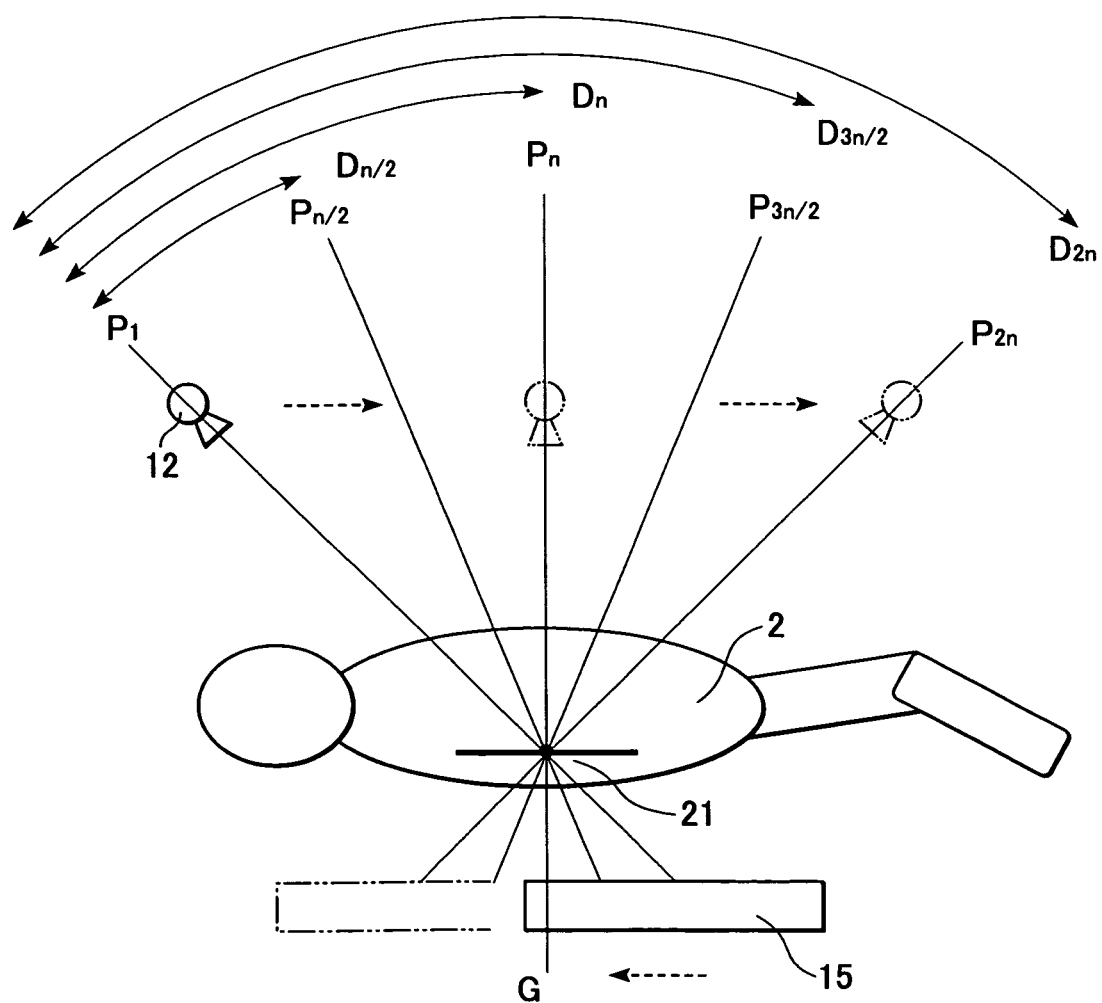
FIG. 5 is a schematic diagram illustrating the details of digital image data.

The above-described image signals $A_i$, that were read after the X-ray exposure, become the sum of the electrical charges that were accumulated by all the X-ray irradiations performed during the interval from when the imaging was started until the latest X-ray irradiation was performed, as in the case of the known analog-tomographic imaging. Therefore, as shown in FIG. 5, the digital image data $D_i$ becomes the sum of the image data obtained by all the irradiations, including the latest X-ray irradiation. Therefore, the image data $D_i$ becomes the tomographic image data as of the present point in time. Further, it is determined whether or not processing on the basis of X-ray exposure performed at the position $P_{2n}$, which is the last irradiation position, was finished. If the answer is no, the process goes back to step S2. Otherwise, the tomographic imaging is ended (step S6). According to the flow of the tomographic imaging, the processing procedures at steps S2 to S5 are performed 2n times. The i-th ($1 \leq i \leq 2n$), processing procedures are performed, corresponding to the position $P_i$ ($1 \leq i \leq 2n$) of the X-ray tube 12. Subsequently, digital image data $D_{2n}$ is obtained by non-destructive reading performed at the position $P_{2n}$. This digital image data $D_{2n}$ becomes the latest tomographic image data.

Thus, the X-ray-digital-tomographic imaging is performed in the above-described manner.

Next, a method of processing image data will be described.

In this embodiment, the operator determines whether or not a tomographic image obtained by each X-ray pulse irradiation should be displayed in real time and whether or not the latest tomographic image should be displayed, through the imaging-condition setter 5. In this embodiment, each of tomographic images is displayed in real time until the latest tomographic image is displayed. In this case, instructions about this setting are transmitted from the imaging controller 3 to the image-process designator 74. Upon receiving these instructions, the image-process designator 74 controls the image memory 71 and the gray-scale adjustor 73 as below.

The image data $D_i$ is transmitted to the image memory 71, and stored therein. The image data $D_i$ is further transmitted to the monitor 8 via the gray-scale adjuster 73 in real time and at the instant when it is stored in the image memory 71. Subsequently, tomographic images $M_1$ to $M_{2n}$ of the subject 2 corresponding to the image data $D_1$ to $D_{2n}$, are sequentially displayed in real time for each X-ray exposure on the monitor 8. Therefore, it becomes possible to monitor the change of the state of the tomographic images displayed on the monitor 8 in real time during imaging. That is to say, the tomographic images includes the tomographic image $M_1$ obtained by oblique imaging performed when the X-ray tube 12 is at the position $P_1$ and other tomographic images with higher quality. It becomes also possible to monitor the latest tomographic image soon after the X-ray tube 12 finishes X-ray irradiation at the position P2n.

The tomographic images $M_1$ to $M_{2n}$, that are displayed, are formed of the image data $D_1$ to $D_{2n}$ that had been subjected to gray-scale process by the gray-scale adjuster 73. Therefore, the change of the state of the images displayed in sequence can be clearly monitored.

Figure 6:
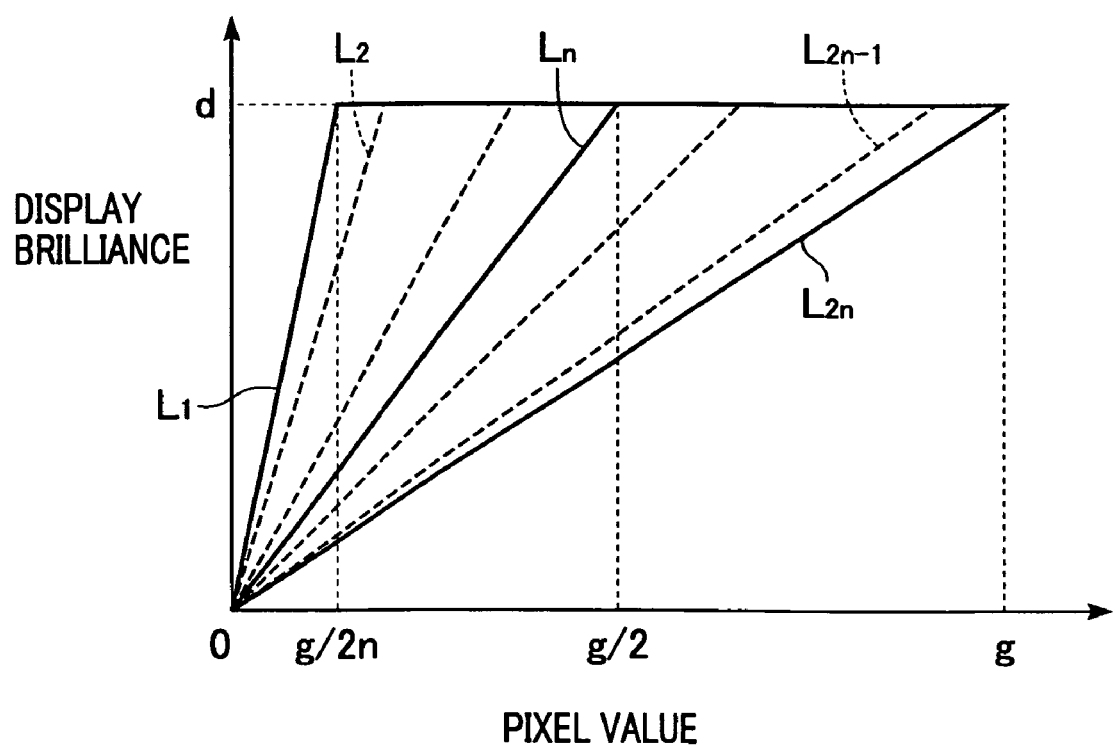
FIG. 6 is a graph illustrating an example lookup table.

There is provided a reference table illustrating how the value of pixels of the image data is converted so that the image is displayed with predetermined brilliance on the monitor 8. Hereinafter, the reference table will be referred to as a lookup table or an LUT. In this embodiment, LUT information is prepared for each of the image data. FIG. 6 shows an example LUT.

In FIG. 6, the LUT information designated by reference numeral $L_{2n}$ is used for displaying the latest tomographic image data $D_{2n}$. In this case, minimum brilliance value 0 and maximum brilliance value d correspond to minimum pixel value 0 and maximum pixel value g, respectively, so that a linear gray-scale conversion characteristic can be presented. Although the maximum pixel value g corresponds to the maximum brilliance value d, it may be arranged that the maximum pixel value g corresponds to the minimum brilliance value 0.

The LUT information designated by reference numeral $L_1$ is used for displaying the first tomographic image data $D_1$. In this case, the minimum brilliance value 0 and the maximum brilliance value d correspond to the minimum pixel value 0 and pixel value g/2n, respectively, so that the gray-scale conversion characteristic becomes linear as long as the pixel value is less than g/2n. If the pixel value becomes g/2n or more, it is arranged that the maximum brilliance value d corresponds thereto.

The LUT information designated by reference numeral $L_i$ is used for displaying the tomographic image data $D_i$. In this case, the minimum brilliance value 0 and the maximum brilliance value d correspond to the minimum pixel value 0 and pixel value gi/2n, respectively, so that the gray-scale conversion characteristic becomes linear as long as the pixel value is less than gi/2n. If the pixel value becomes gi/2n or more, it is arranged that the maximum brilliance value d corresponds thereto. The inclination of the linear parts of the above-described LUT information changes, as shown in FIG. 6.

Since the tomographic images are displayed by using the 2n types of LUT information, the concentration of an image obtained in an early stage of the tomographic imaging does not become low. Further, since this embodiment allows for displaying a tomographic image with high contrast at any stage of the tomographic imaging, it becomes easier to monitor the change in the states of the displayed images.

In the past, in the case where known digital-tomographic imaging is performed, the imaging is performed in sequence by using X-ray pulses. That is to say, the destructive reading is performed in sequence. In this case, the correctness of each of the obtained images is reduced due to imaging performed just before the last imaging, that is, a so-called after image. This problem occurs in the case where unread electrical charges remain after the destructive reading is performed, the interval from when imaging is finished and the next imaging is started is short, for example, and the remaining unread electrical charges hardly decrease in number.

According to this embodiment, however, the electrical signals are read by the non-destructive reading method. Accordingly, it becomes possible to avoid the above-described problem that occurred in the past due to the above-described remaining electrical charges. Since the configuration of this embodiment is not affected by the after image, it becomes possible to obtain a correct image at all times.

It may be arranged that X-rays are irradiated in sequence during tomographic imaging instead of using a plurality of X-ray pulses. Further, it may be arranged that an electrical signal from the solid-image pickup unit 13, where the electrical signal is obtained after the last X-ray irradiation, is read by the destructive-reading method instead of the non-destructive reading method.

Further, it may be arranged that only one type of LUT information is used for the plurality of image data Di, where the image data Di is obtained in sequence. That is to say, there is no need to prepare as many types of LUT information as the number of times the X-ray exposure is performed. Further, the function, that is, a gray-scale adjustment function, is not limited to the above-described embodiment, but can be determined by the operator according to their needs. Further, it may be arranged that the gain of the amplifier 141, where the gain is used when the read electrical signals are amplified, is set in a changeable manner. That is to say, the gain may be set so as to be changed according to the number of times the X-ray exposure is performed, the X-ray-irradiation amount, and so forth. Accordingly, it becomes possible to obtain the same effect as that of the first embodiment by using only one type of LUT information.

In the case where the operator determines that at least one tomographic image with suitable quality is obtained before X-ray irradiation is performed 2n times while the operator monitors tomographic images displayed on the monitor 8 in sequence and in real time, the operator may stop imaging then. In this case, the operator turns on the imaging end switch 32. Subsequently, an imaging end instruction is transmitted from the imaging controller 3 to the X-ray controller 4, whereby the X-ray irradiation from the X-ray tube is stopped. Since the time required for the tomographic imaging is reduced, it becomes possible to prevent the subject 2 (the human body or the like) from being unnecessarily exposed to X-rays.

Further, it may be arranged that the tomographic image data being stored in the memory 71 is deleted after image display is performed, whereby the memory capacity can be reduced.

Further, the method of processing the obtained digital image data is not limited to the above-described embodiment. Another method of processing the obtained digital image data will be described with reference to FIG. 1.

In the case where the X-ray-tomographic imaging apparatus of this embodiment is used, it becomes possible to perform subtraction or addition between and/or among arbitrary data of the image data $D_1$ to $D_{2n}$ stored in the image memory 71 for each pixel. It becomes also possible to display the image data on the monitor 8 and store the image data in the image memory 71 again. Therefore, it becomes possible to reorganize a tomographic image in an arbitrary imaging angle range and/or a projection image from a predetermined direction by performing calculations a relatively small number of times.

Figure 7:
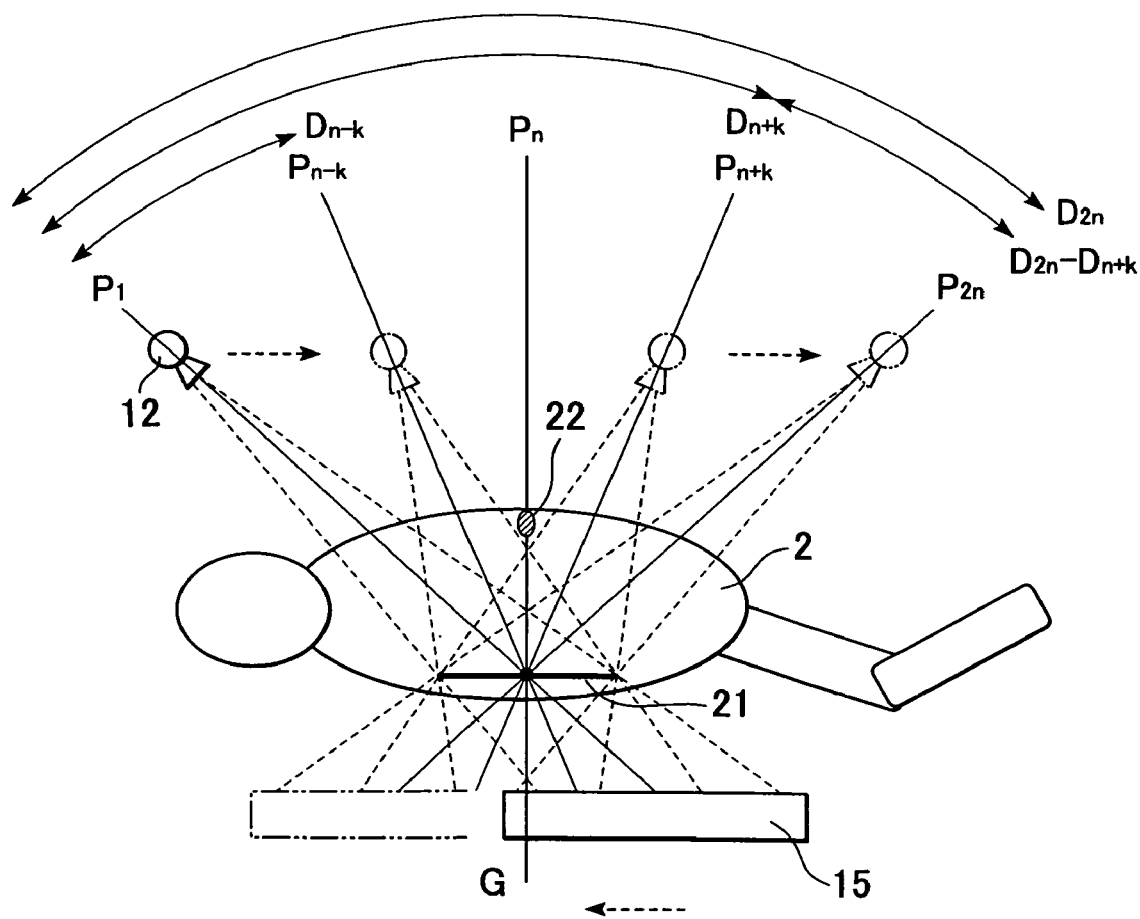
FIG. 7 is a schematic diagram illustrating the relationship between a metal piece and the details of the digital image data.

For example, as shown in FIG. 7, tomographic image data obtained by a calculation shown as $(D_{n-k})+(D_{2n}-D_{n+k})$ does not include tomographic image data obtained by X-ray irradiation performed during the time the X-ray tube 12 moves from position $P_{n-k+1}$ to position $P_{n+k}$. Further, it becomes possible to reorganize a tomographic image without using part of the image data obtained by the tomographic imaging in the case where a foreign body, such as a metal piece 22 in the subject 2, is not on the tomographic section 21, but at a predetermined position near the X-ray-tube 12, as shown in FIG. 7. Subsequently, the tomographic image is not affected by the foreign body, such as the metal piece 22. That is to say, a correct tomographic image can be obtained.

Further, difference between and/or among image data for each pixel, where the image data is obtained by non-destructive reading performed in sequence during the tomographic imaging, can be obtained by calculations $D_{2n}-D_{2n-1}$, $D_n-D_{n-1}$, and so forth. This difference data is equivalent to the image data obtained by oblique imaging or normal imaging performed when the X-ray tube 12 is at the positions $P2_n$, $P_n$, and so forth. Since the above-described calculations allow for obtaining the difference between and/or among the image data obtained by non-destructive reading consecutively performed two times, it becomes possible to obtain image data that is the same as image data that is obtained by the known digital tomographic imaging, and that is not yet subjected to reorganization.

(Second Embodiment)

A second embodiment of the present invention will now be described. The configuration of an X-ray-tomographic imaging apparatus and a method of processing image data according to this embodiment is basically the same as those of the first embodiment. However, imaging conditions and a control method for performing tomographic imaging are different from those of the first embodiment.

As in the first embodiment, the operator sets the tomographic imaging conditions through the imaging-condition setter 5 as a preparation for tomographic imaging. Main conditions among these are, for example, X-ray irradiation conditions including the tube voltage, the tube current, and the X-ray irradiation time, and imaging conditions including the imaging angle range, the number of times imaging is performed, and so forth.

Figure 8:
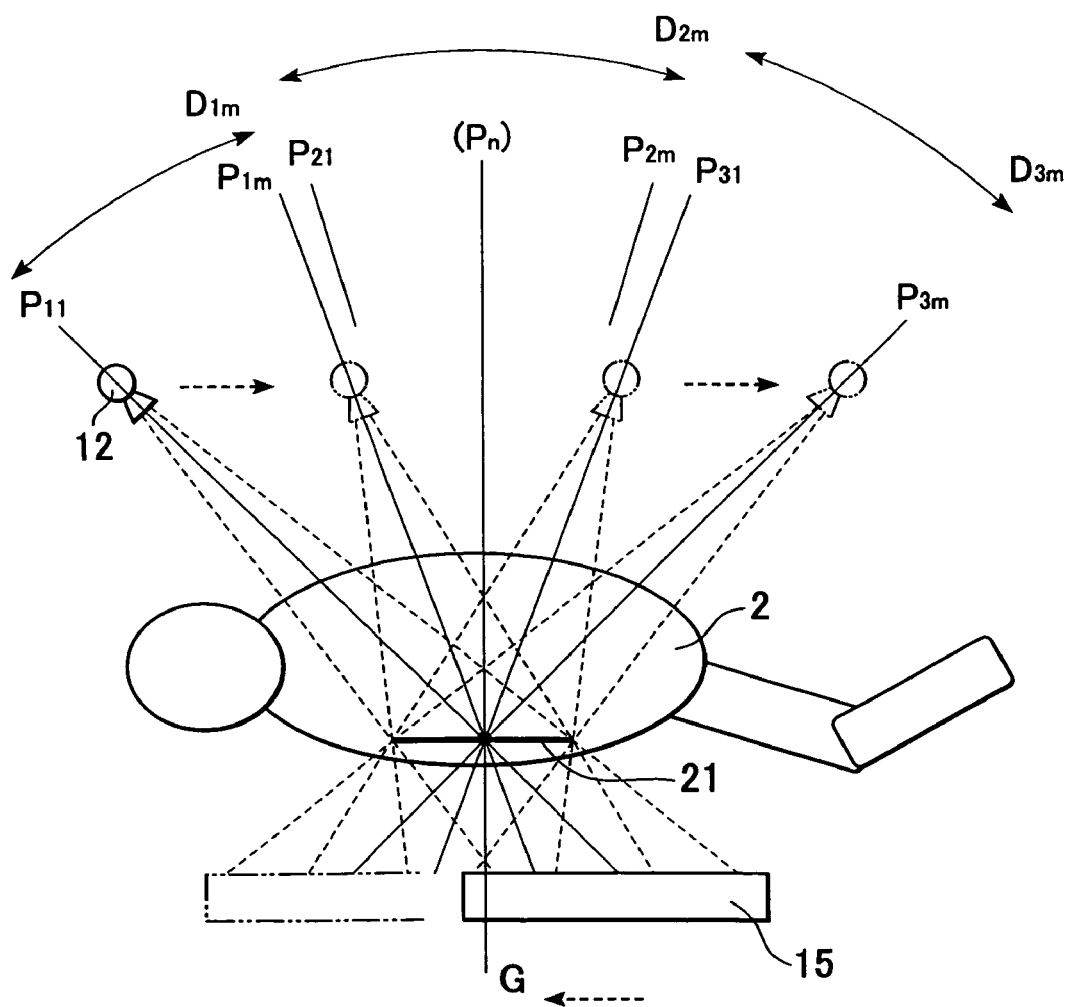
FIG. 8 is a schematic diagram illustrating example imaging conditions according to a second embodiment of the present invention.

FIG. 8 is a schematic diagram illustrating example imaging conditions according to the second embodiment. Under these imaging conditions, the vertical line G passing through the center of the tomographic section 21 is determined to be a center point. Further, a range from −45° to +45° of the subject 2 with respect to the center point along a vertical direction is determined to be the imaging angle range. That is to say, a 90°-angle range of the subject 2 is determined to be the imaging angle range. This imaging angle range is divided into three ranges, that is, first to third imaging ranges. The angle of each of these imaging ranges is about 30°. As for the position of the X-ray tube 12, position $P_{11}$ is determined to be an imaging start point and position $P_{3m}$ is determined to be an imaging end point. The relationship between the position of the X-ray tube 12 and each of the first to third imaging ranges will be described as below. That is to say, the range from the position $P_{11}$ to position $P_{1m}$ corresponds to the first imaging range, the range from position $P_{21}$ to position $P_{2m}$ corresponds to the second imaging range, and the range from position $P_{31}$ to the position $P_{3m}$ corresponds to the third imaging range. Therefore, the tomographic imaging is started when the X-ray tube 12 is at the position P11 and ended when the X-ray tube 12 reaches the position $P_{3m}$. When the subject 2 is subjected to the tomographic imaging, an X-ray pulse is emitted from the positions $P_{11}$, $P_{12}$, . . . , $P_{3m-1}$, and $P_{3m}$. Each of the positions divides a segment from the position $P_{11}$ to the position $P_{3m}$ into $2_{n-1}$ equal portions. Subsequently, the tomographic imaging is performed 2n times (=3m times).

In the case where the abdomen of the subject 2 is subjected to tomographic imaging, it is arranged that the imaging is performed 2n/3 times (=m times) per one imaging angle, for example. The values of the tube voltage V and X-ray irradiation time T are determined to be $V_1$ and $T_1$, as in the first embodiment. However, the value of the tube current I is determined to be $I_3$, that is three times as high as the tube current value $I_1$ of the first embodiment. These conditions remain constant while the X-ray exposure is performed 2n times (=3m times). Under these conditions, the last signal of signals generated by imaging performed in each of the three imaging areas is read by the destructive reading method and the other signals are read by the non-destructive reading method.

Figure 9:
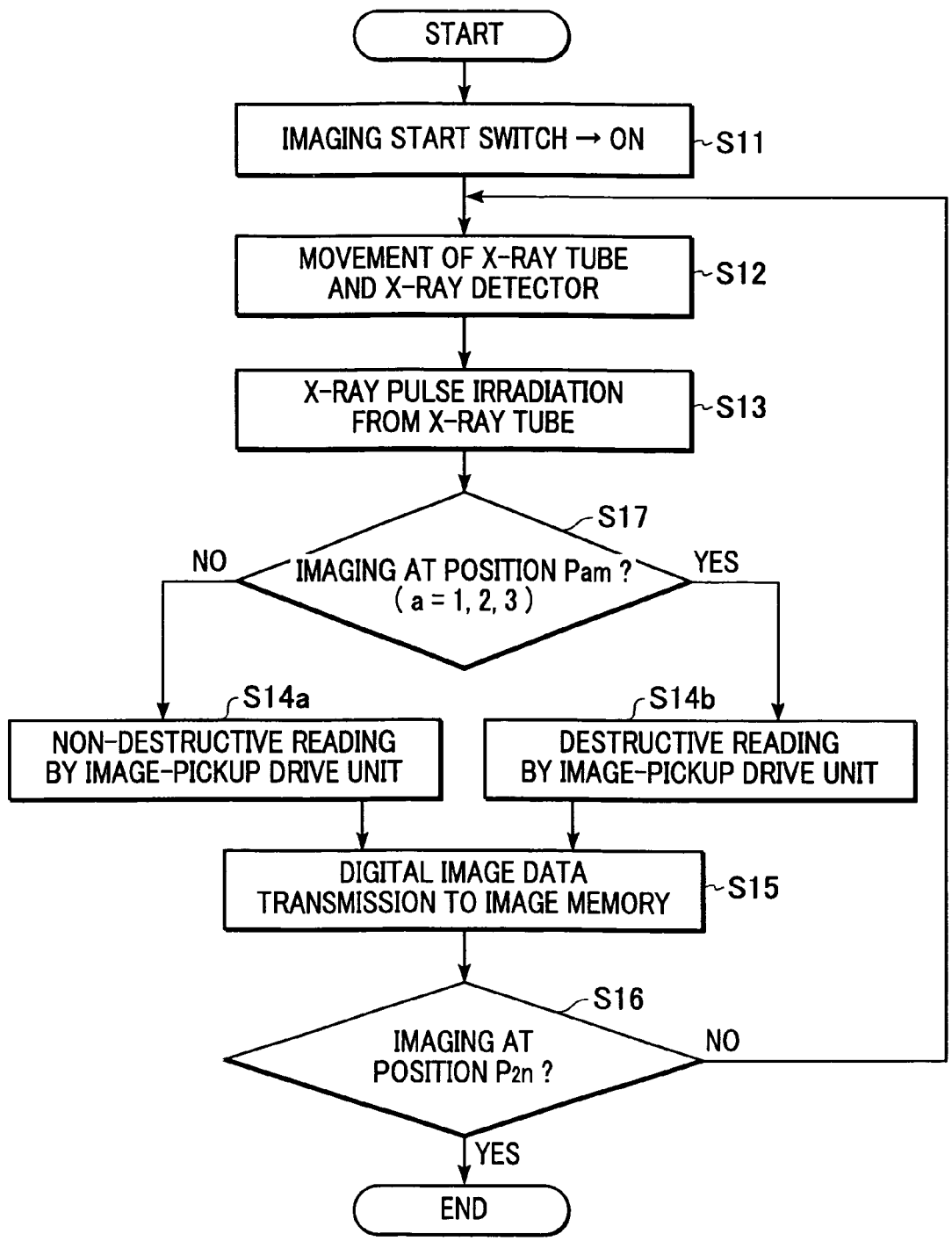
FIG. 9 is a flowchart illustrating an imaging method on the basis of the imaging conditions shown in FIG. 8.

Subsequently, the tomographic imaging is started. According to the flowchart shown in FIG. 9, first, it is determined whether or not the operator turned on the imaging start switch 31. If the answer is yes, the process advances to step S12. If the answer is no, the determination process at step S11 is repeated with predetermined timing. At step S12, the movement of the X-ray tube 12 and the X-ray detector 15 is controlled.

At step S13, an X-ray pulse generated in the case where the value of the tube voltage is $V_1$, the value of the tube current is $I_3$, and the value of the irradiation time is $T_1$, is emitted from the X-ray tube 12 in synchronization with the movement of the X-ray tube 12 and the X-ray detector 15.

When the X-ray pulse irradiation is finished, electrical charges distributed according to an X-ray image generated by X-rays that passed through the subject 2 are read as electrical signals. However, in the first imaging range, a last signal of signals generated by the X-ray exposure performed in the first imaging range, the last signal being generated when the X-ray tube 12 is at the position $P_{1m}$, is read by the destructive reading method (steps S17 and S14b). Other signals generated by the other X-ray exposure, the other signals being generated when the X-ray tube 12 is at the positions $P_{11}$ to $P_{1(m-1)}$, are read by the non-destructive reading method (steps S17 and 14a). Subsequently, image signals $A_{1i}$ corresponding to X-ray irradiation performed during the X-ray tube 12 moves from the position $P_{11}$ to the position $P_{1m}$ are obtained. These image signals $A_{1i}$ correspond to one frame. If an electrical signal $A_{1m}$ is read by the destructive reading method, the major portions of electrical charges in each of the pixels of the solid-image pickup unit 13 are lost.

The electrical signals read within the first imaging range are amplified according to a predetermined gain of the amplifier 141 and converted to digital signals by the A/D converter 142. Then, the adder 144 applies predetermined information to the digital signals, that is, digital image signals corresponding to one frame, whereby digital image data $D_{1i}$ is generated. This digital image data $D_{1i}$ is transmitted to the image memory 71 and stored therein at step S15.

At step S16, it is determined whether or not process on the basis of X-ray exposure performed at the position $P_{3m}$, which is the last irradiation position, was performed. If the determination result is no, the process goes back to step S12. After that, tomographic imaging is performed in the second imaging area. As in the case of the first imaging area, a last signal of signals generated by the X-ray exposure performed in the second imaging area, the last signal being generated when the X-ray tube 12 is at the position $P_{2m}$, is read by the destructive reading method (steps S17 and S14b). Other signals generated by the other X-ray exposure, the other signals being generated when the X-ray tube 12 is at the positions $P_{21}$ to $P_{2(m-1)}$, are read by the non-destructive reading method (steps S17 and 14a). After that, tomographic imaging is performed in the third imaging area via step S16, as in the first embodiment.

After that, processing procedures relating to X-ray irradiation performed at the position $P_{3m}$, which is the last imaging position, are performed, whereby the tomographic imaging is ended (step S16).

According to the above-described tomographic imaging method, digital image data $D_{11}$ to $D_{3m}$, corresponding to 2n (=3m) frames, is stored in the image memory 71, as in the first embodiment. In this embodiment, image data obtained by calculation, shown as $D_{1m}+D_{2m}+D_{3m}$, becomes final tomographic image data. Since the current of the X-ray tube 12 is three times as high as that of the first embodiment, the amount of X-ray irradiation also becomes three times as high as that of the first embodiment. Accordingly, a tomographic image with quality higher than that of the first embodiment can be obtained.

As has been described, according to the present invention, it becomes possible to obtain image data on the tomographic section of a subject with efficiency and effectiveness.

(Other Embodiments)

It is to be understood that the object of the present invention can also be achieved by supplying a storage medium storing program code of software for implementing the functions of the apparatus or system, according to the first or second embodiment, to an apparatus or system so that a computer (CPU, MPU, etc.) of the apparatus or system reads and executes the program code stored in the storage medium.

In that case, the program code itself, read from the storage medium, achieves the functions of the first or second embodiment, and thus the storage medium storing the program code and the program code itself constitute the present invention.

The storage medium for providing the program code may be, for example, a ROM, a floppy (registered trademark) disk, a hard disk, an optical disk, a magneto-optical disk, a CD-ROM, a CD-R, a magnetic tape, a non-volatile memory card, etc.

Furthermore, not only by the computer reading and executing the program code, but also by the computer executing part of or the entire process utilizing an OS, etc. running on the computer based on instructions of the program code, the functions of the first or second embodiment may be achieved. The latter is also one of embodiments of the present invention.

In another embodiment of the present invention, the program code read from the storage medium may be written to a memory of a function extension board inserted in the computer or a function extension unit connected to the computer. The functions of the first or second embodiment may be realized by executing part of or the entire process by a CPU, etc. of the function extension board or the function extension unit based on instructions of the program code.

When the present invention is applied to a program or a storage medium storing the program, it is to be understood that the present invention may also be applied to a system including a plurality of apparatuses (e.g., radiation generating apparatuses, radiographic apparatuses, image processing apparatuses, and interface apparatuses, etc.) and to a single apparatus in which functions of these apparatuses are integrated. When the present invention is applied to a system including a plurality of apparatuses, the apparatuses communicate with one another via, for example, electrical, optical, and/or mechanical means, and/or the like.

Furthermore, the present invention may also be applied to an image diagnosis aiding system including a network (LAN and/or WAN, etc).

The present invention thus achieves the above-described objective.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An X-ray-tomographic imaging method used for an X-ray-tomographic imaging apparatus having a solid-image pickup unit that can convert an X-ray projection image to a signal and read the signal in a non-destructive reading manner, the X-ray-tomographic imaging apparatus being provided for obtaining image data of a predetermined tomographic section in a subject by using a plurality of X-ray projection images achieved by a plurality of X-rays that is made incident on the predetermined tomographic section from different directions, the X-ray imaging method comprising the steps of:

performing accumulation control for making the solid-image pickup unit accumulate the signal of each of the X-ray projection images; and performing read control for making the solid-image pickup unit read the signal in a non-destructive reading manner during the signal accumulation.

2. A program that can be executed by an information processing apparatus having program code for practicing the X-ray-tomographic imaging method according to claim 1.

* * * * *